United States Patent
Pfleiderer et al.

(10) Patent No.: US 10,589,074 B2
(45) Date of Patent: Mar. 17, 2020

(54) MAGNETO-RESISTIVE SENSOR TOOL SET FOR HYDROCEPHALUS VALVE

(71) Applicant: INTEGRA LIFESCIENCES SWITZERLAND SÀRL, Le Locle (CH)

(72) Inventors: Martin Pfleiderer, Raynham, MA (US); Toralf Bork, Raynham, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 302 days.

(21) Appl. No.: 15/443,521

(22) Filed: Feb. 27, 2017

(65) Prior Publication Data

US 2018/0243542 A1    Aug. 30, 2018

Related U.S. Application Data

(60) Provisional application No. 62/356,775, filed on Jun. 30, 2016.

(51) Int. Cl.
*A61M 27/00* (2006.01)

(52) U.S. Cl.
CPC .................. *A61M 27/006* (2013.01)

(58) Field of Classification Search
CPC .................................. A61M 27/006
See application file for complete search history.

(56) References Cited

U.S. PATENT DOCUMENTS

| | | |
|---|---|---|
| 3,902,252 A | 9/1975 | Farber |
| 4,173,228 A | 11/1979 | Van Steenwyk et al. |
| 4,595,390 A | 6/1986 | Hakim et al. |
| 4,608,992 A | 9/1986 | Hakim et al. |
| 4,622,644 A | 11/1986 | Hansen |
| 4,839,809 A | 6/1989 | Leighton et al. |
| 5,309,096 A | 5/1994 | Hoegnelid |
| 5,425,382 A | 6/1995 | Golden et al. |
| 5,435,070 A | 7/1995 | Kilian |
| 5,438,990 A | 8/1995 | Wahlstrand et al. |
| 5,525,901 A | 6/1996 | Clymer et al. |
| 5,643,194 A | 7/1997 | Negre |
| 5,709,225 A | 1/1998 | Budgifvars et al. |
| 5,758,667 A | 6/1998 | Slettenmark |
| 5,879,297 A | 3/1999 | Haynor et al. |
| 5,944,023 A | 8/1999 | Johnson et al. |
| 6,101,417 A | 8/2000 | Vogel et al. |
| 6,129,668 A | 10/2000 | Haynor et al. |

(Continued)

OTHER PUBLICATIONS

Extended European Search Report issued in European Patent Application No. 17178766.6 dated Nov. 21, 2017.

*Primary Examiner* — Benjamin J Klein
(74) *Attorney, Agent, or Firm* — Troutman Sanders LLP (57) ABSTRACT

A locator as part of a toolkit for locating an implanted valve. The locator is used in concert with an indicator that nests therein. The locator has a lower ring with a contact surface, contacting a patient, a key positioning the nested indicator to prevent rotation, and a lower ring joint opposite the contact surface. Also included is an upper ring with an upper ring joint rotatingly interfacing with the lower ring joint, a flow direction identifier, and a flow setting identifier. Further, the upper and the lower rings rotate relative to each other, and the lower ring is floor-less.

20 Claims, 7 Drawing Sheets

(56) References Cited

U.S. PATENT DOCUMENTS

| | | |
|---|---|---|
| 6,138,681 A | 10/2000 | Chen et al. |
| 6,216,028 B1 | 4/2001 | Haynor et al. |
| 6,230,038 B1 | 5/2001 | von Gutfeld et al. |
| 6,242,907 B1 | 6/2001 | Clymer et al. |
| 6,263,230 B1 | 7/2001 | Haynor et al. |
| 6,439,538 B1 | 8/2002 | Ito |
| 6,485,449 B2 | 11/2002 | Ito |
| 6,505,062 B1 | 1/2003 | Ritter et al. |
| 6,690,159 B2 | 2/2004 | Burreson et al. |
| 6,702,249 B2 | 3/2004 | Ito |
| 6,707,293 B2 | 3/2004 | Wan et al. |
| 6,882,146 B2 | 4/2005 | Maiwald |
| 6,891,367 B2 | 5/2005 | Shinmura et al. |
| 6,937,906 B2 | 8/2005 | Terry et al. |
| 7,126,331 B2 | 10/2006 | Johnson et al. |
| 7,173,419 B1 | 2/2007 | Johnson et al. |
| 7,197,354 B2 | 3/2007 | Sobe |
| 7,228,252 B2 | 6/2007 | Alexander et al. |
| 7,301,332 B2 | 11/2007 | Govari et al. |
| 7,334,582 B2 | 2/2008 | Bertrand et al. |
| 7,525,309 B2 | 4/2009 | Sherman et al. |
| 7,753,913 B2 | 7/2010 | Szakelyhidi, Jr. et al. |
| 7,842,004 B2 | 11/2010 | Kassem |
| 7,856,987 B2 | 12/2010 | Bertrand et al. |
| 8,015,977 B2 | 9/2011 | Bertrand et al. |
| 8,038,641 B2 | 10/2011 | Soares et al. |
| 8,089,276 B2 | 1/2012 | Kentsch |
| 8,148,978 B2 | 4/2012 | Sherman et al. |
| 8,241,240 B2 | 8/2012 | Murphy |
| 8,257,296 B2 | 9/2012 | Bertrand et al. |
| 8,398,617 B2 | 3/2013 | Ginggen et al. |
| 8,424,393 B1 | 4/2013 | Lee |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 | 1/2014 | Bertrand et al. |
| 8,630,695 B2 | 1/2014 | Negre et al. |
| 8,753,331 B2 | 6/2014 | Murphy |
| 8,836,458 B2 | 9/2014 | Lee |
| 8,862,200 B2 | 10/2014 | Sherman et al. |
| 9,149,615 B2 | 10/2015 | Wilson |
| 9,216,275 B2 | 12/2015 | Soares et al. |
| 9,220,876 B2 | 12/2015 | Girardin et al. |
| 9,242,077 B2 | 1/2016 | Wilson et al. |
| 9,872,972 B2 | 1/2018 | Soares et al. |
| 2004/0017192 A1 | 1/2004 | Clymer et al. |
| 2004/0055610 A1 | 3/2004 | Forsell |
| 2004/0064030 A1 | 4/2004 | Forsell |
| 2004/0097803 A1 | 5/2004 | Panescu |
| 2004/0250820 A1 | 12/2004 | Forsell |
| 2006/0124140 A1 | 6/2006 | Forsell |
| 2007/0276218 A1 | 11/2007 | Yellen |
| 2008/0048635 A1 | 2/2008 | Hughes |
| 2008/0297145 A1 | 12/2008 | Mahr et al. |
| 2009/0275924 A1 | 11/2009 | Lattanzio et al. |
| 2010/0010338 A1 | 1/2010 | van Dam et al. |
| 2010/0292759 A1 | 11/2010 | Hahn et al. |
| 2011/0031961 A1 | 2/2011 | Durand et al. |
| 2011/0105992 A1 | 5/2011 | Girardin et al. |
| 2012/0041297 A1 | 2/2012 | McGary |
| 2012/0083856 A1 | 4/2012 | Thacker et al. |
| 2013/0245402 A1 | 9/2013 | Ziaie et al. |
| 2015/0094643 A1* | 4/2015 | Soares ............... A61M 27/006 604/9 |

\* cited by examiner

MAGNETO-RESISTIVE SENSOR TOOL SET FOR HYDROCEPHALUS VALVE

CROSS-REFERENCE TO RELATED APPLICATIONS

This application claims priority to U.S. Provisional Application Ser. No. 62/356,775 filed Jun. 30, 2016. The provisional application is incorporated herein by reference.

FIELD OF THE INVENTION

The invention relates generally to surgically implantable fluid drainage systems. More specifically, the invention relates to extracorporeal tools for locating and adjusting the adjustable valves used for cerebrospinal fluid drainage.

BACKGROUND

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream. Typically, the shunt valve is palpatable by the physician through the patient's skin after implantation. The shunt valves, which can have a variety of configurations, can be designed to allow adjustment of their fluid drainage characteristics after implantation.

It is also important to be able to externally read or verify the setting of the valve. With some adjustable valves, x-ray images are used to determine the current setting of the valve, before and after adjustment. With other adjustable valves, the orientation of a rotor in the valve can be read magnetically, using a magnetic compass-like device positioned above the valve, outside the skin of the patient. In examples, both the adjuster and the indicator are used in conjunction with a locator. The locator tool is used in the process of determining the location of the valve under the skin and subsequently to maintain this established position. The adjuster and the indicator tools engage within the locator tool to perform their function.

The locator can be placed by palpitating the skin of the patient and aligning a cut out of the valve in the base of the locator. Once placed, the shape of the valve indicates the flow direction, from which the orientation of the valve setting is based. Another type of valve can have an additional marker magnet to allow for the magnetic identification of the flow direction, making it unnecessary to palpitate to locate the valve's direction.

However the locator tool is nevertheless required for proper placement and use of the Adjustment tool. A magneto-resistive sensor based indicator tool needs to be zeroed at a distance of at least 10 to 15 cm from the valve in order to take into account the earth magnetic field. Each time the locator's absolute orientation is changed during use, a new zeroing becomes necessary. This is time consuming. Thus, it is desirable that the locator tool can be turned and aligned with the valve's flow direction whilst maintaining the indicator tool's absolute orientation.

SUMMARY

Examples of the present invention include a locator as part of a toolkit for locating an implanted valve. The locator is used in concert with an indicator that nests therein. The locator has a lower ring with a contact surface, contacting a patient, a key positioning the nested indicator to prevent rotation, and a lower ring joint opposite the contact surface. Also included is an upper ring with an upper ring joint rotatingly interfacing with the lower ring joint, a flow direction identifier, and a flow setting identifier. Further, the upper and the lower rings rotate relative to each other, and the lower ring is floor-less. Another example of the locator where the lower ring further includes a telescoping section expanding and collapsing a height between the contact surface and the lower ring joint and the telescoping section only moves vertically.

Another example of the invention is a method of using a toolkit for locating the implanted valve. The toolkit has a locator with an upper and a lower ring rotatably engaged to each other, and an indicator and an adjustor that nest within the locator. The steps include placing the locator generally over the implanted valve, nesting the indicator in the locator, centering the locator and the indicator over the implanted valve, determining a flow direction and a valve setting of the implanted valve, and rotating an outer ring of the locator to match the determined flow direction and valve setting while maintaining a position of the lower ring.

The method also has the step of zeroing the indicator at a distance from the implanted valve prior to the nesting step. Another example has the steps of telescoping the locator after the nesting step, zeroing the indicator at a distance from the implanted valve, and collapsing the locator after the zeroing step and before the centering step. Also, removing the indicator from the locator, disposing the adjustor in the locator oriented to the determined valve setting, and adjusting the valve setting to a new valve setting by rotating the adjustor.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Methods and integrated tools of the present invention enable a physician to consistently and reliably locate an implantable, magnetically settable valve (valve) and change a setting of (adjust) the valve from a current setting to a target setting without interference from the valve. In an example, the valve is used to control, via its setting, at least one of CSF drainage flow and pressure for a patient with hydrocephalus, is implanted under a patient's scalp or another portion of the patient's skin, and is adjustable from outside (above) the patient's skin but needs to be located.

Other tools and methods for extracorporeally reading and adjusting a hydrocephalus valve are disclosed in U.S. Pat. No. 8,038,641 entitled "Tools and Methods for Programming an Implantable Valve", which is hereby incorporated by reference in its entirety. Within the scope of the present invention, features of the various examples disclosed herein can be used in any combination to construct additional integrated tools and methods for reading and adjusting an implantable valve.

Figures 1, 2, 3:
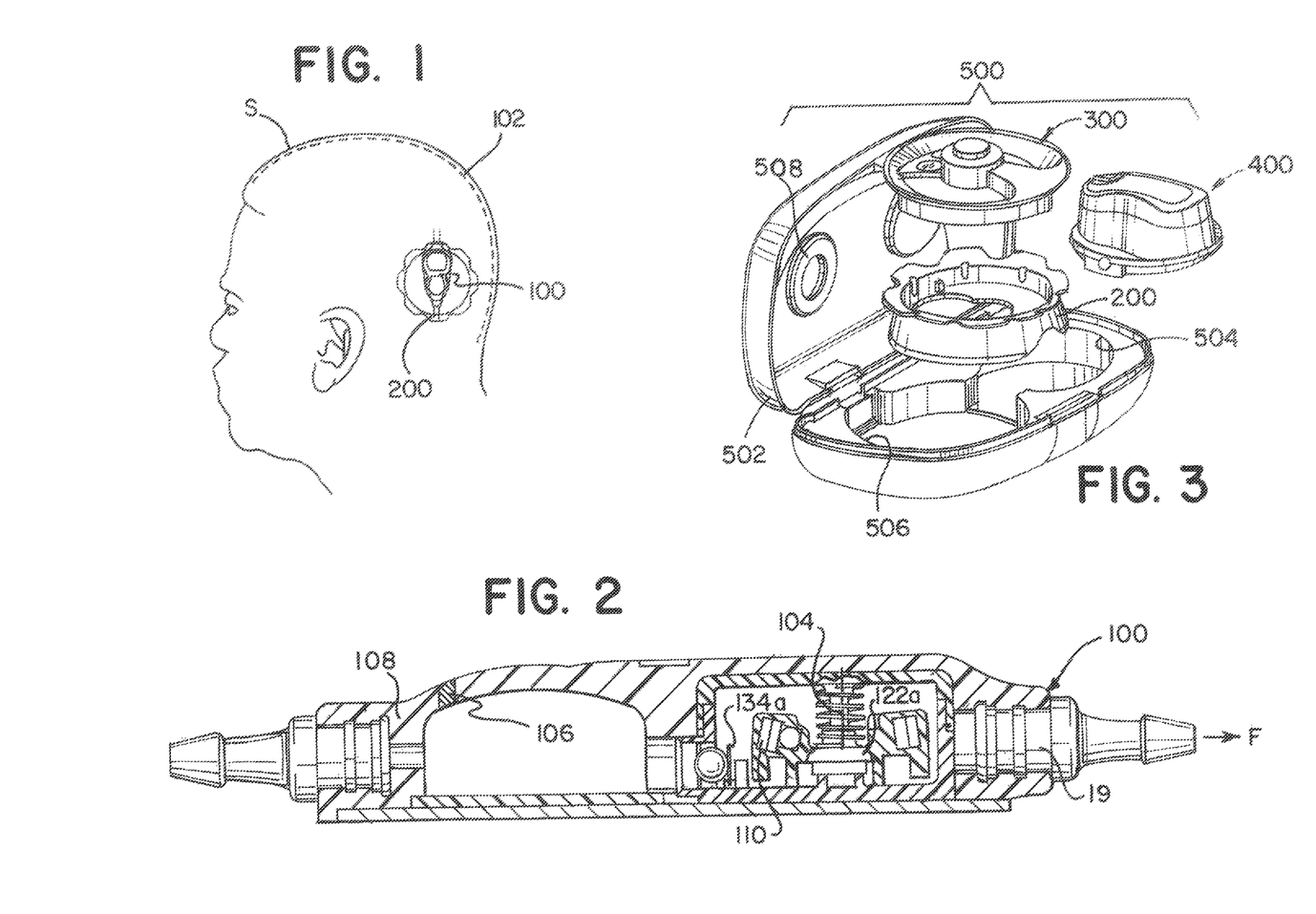
FIG. 1 is an illustration of a typical magnetically oriented valve implanted in a patient.
FIG. 2 is a side cross-sectional view of a typical magnetically oriented valve according to the present invention.
FIG. 3 is a perspective view of a tool set according to the present invention including an indicator tool, a locator tool, and a setting adjuster tool.

FIGS. 1 and 2 illustrate a generalized implantable valve 100 implanted beneath a patient's skin 102. The valve 100 includes a magnetic axis 104 which is the point of reference used to adjust the valve 100 or determine its settings. In an example, the valve 100 has a plurality of predetermined settings corresponding to a plurality of predetermined flows and pressures. In an example, the plurality of settings comprises eight settings.

It is to be understood that the valve 100 can be any magnetically orientated, settable, implantable valve having a magnetically rotatable rotor 110. In an embodiment, the valve 100 is unlocked for rotation about the magnetic axis 104 by a displacement of the rotor 110 along the axis 104, the displacement provided by application an attractive magnetic field along the axis 104. In a further embodiment, the attractive magnetic field and the magnetic field for rotating the rotor about the axis are provided by a single magnetic source that can be either a permanent magnet or an electromagnet.

Further, the valve 100 can be provided with a fixed magnetic marker 106 embedded in a wall 108 of the valve 100 in a vicinity of an end portion to indicate the flow direction F of the valve 100. The fixed magnetic marker 106 can be a permanent magnet piece and, in an example, magnetized in a direction orthogonal to the wall 108. The fixed magnetic marker 106, in an example, can be provided at a position as remote as possible from the magnetic axis 104 to minimize magnetic influence of the marker 106 on the rotor 110 and thus, the settings, and the readings thereof.

FIG. 1 illustrates the valve 100 implanted under the skin 102 of a patient's skull S. Once implanted, the valve is under the skin and typically covered by hair. FIG. 3 now illustrates a magneto-resistive sensor toolset 500 according to the present invention, for locating, identifying settings and adjusting the valve 100. The tool set includes a locator 200, an indicator 300, and an adjustor 400 and each are described below in turn. The indicator tool 300 and the adjuster tool 400 each can nest on top of locator tool 200 as shown and described in more detail below. As illustrated, the toolset 500 can include, as an example, a storage and transport case 502 having a smaller recess 504 for carrying the adjuster 400 and a larger recess 506 for carrying the indicator 300 nested with locator 200. Preferably, portions of the indicator 300 are received within upper recess 508 when case 502 is closed for storage or transport of toolset 500.

Figures 4, 5A:
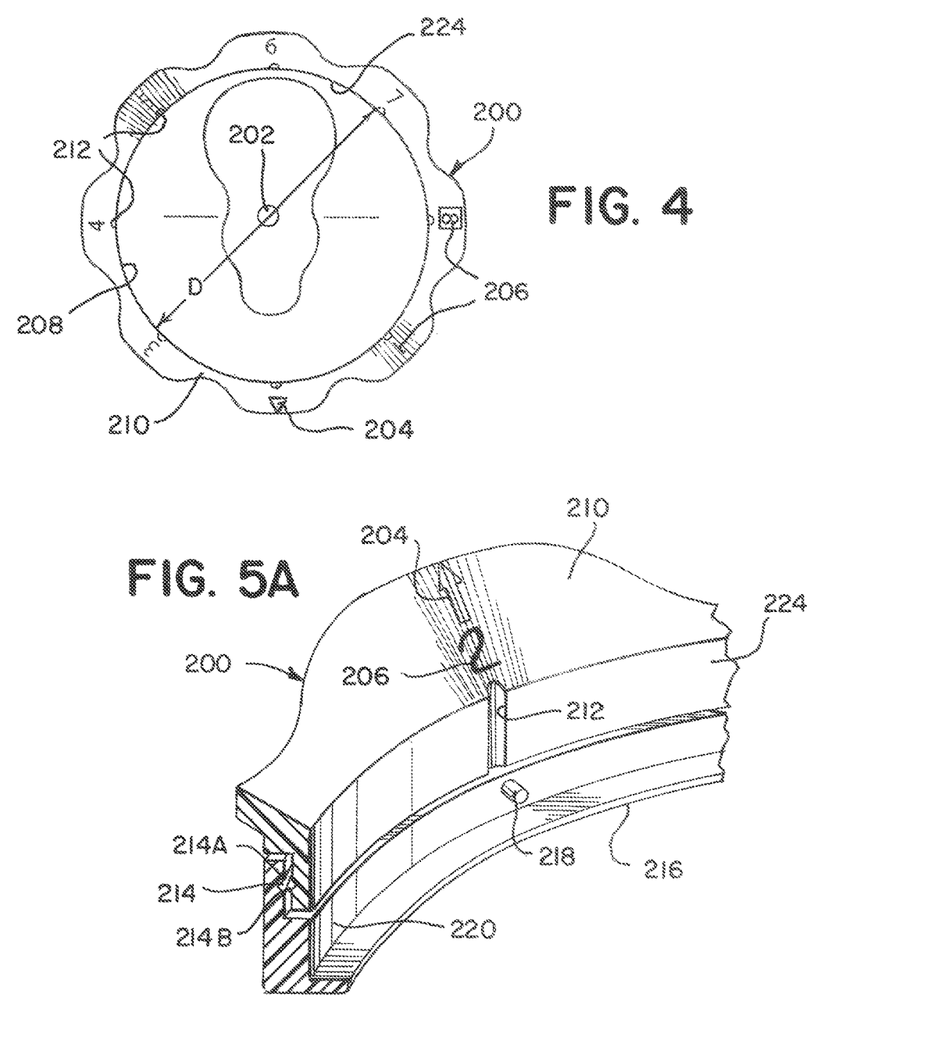
FIG. 4 is a top view of an example of a locator.
FIG. 5A is a partial perspective cross-section of an example of the locator of the present invention.

FIG. 4 illustrates an example of the locator 200. The locator 200 can be typically circular with a center 202 and can have a diameter D. In this example, the locator 200 can be a ring and does not have a floor/barrier/membrane in its inner diameter. While an example can be circular, the locator 200 can have any shape to allow an adjustor and/or indicator to perform their functions. Thus, in one example, the locator 200 can be non-circular and composed of numerous line segments.

The locator 200 can also have a flow direction indicator 204, and flow setting indicators 206. Both can be visual markings without or with petals or tabs extending outside a first perimeter 208 defined by the diameter D (wherein first perimeter 208 can equal πxdiameter D). The flow direction identifier 204 can be an arrow, and that arrow is aligned with the direction of fluid flow F through the implanted valve 100. The flow setting indicators 206 can be visual markings denoting the setting of the valve 100, i.e. in some examples, the position of the rotor 110.

Figure 5B:
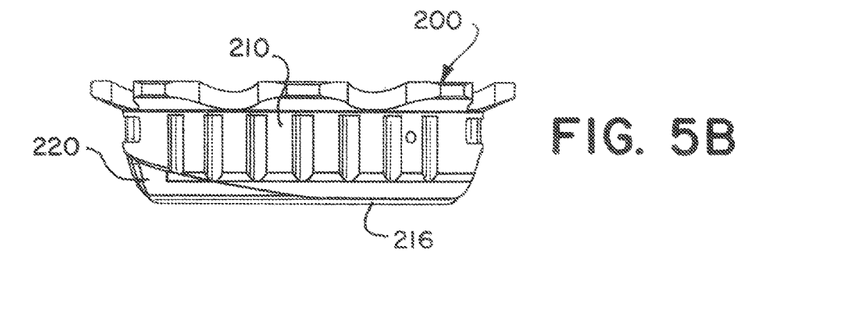
FIGS. 5B and 5C are a side view of the locator collapsed and expanded at the telescope section.
Figure 5C:
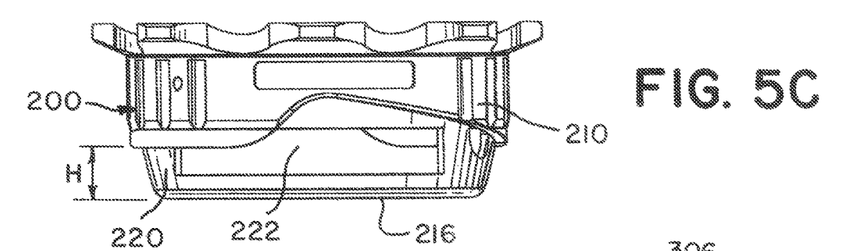

FIGS. 5A-5C illustrate different views of an example of the locator 200. FIG. 5*a* illustrates a partial perspective cross-section of the locator 200 while FIGS. 5B and 5C illustrate the collapsed and expanded versions of the locator 200. The locator 200 can be made of two interfacing rings 210, 220. The outer/upper ring 210 and the lower/inner ring 220 can rotate relative to as well as displace vertically from one another. The outer ring 210 can have both the flow direction identifier 204 and flow setting indicators 206. Further, the outer ring 210 can have a rotation stop 212, i.e. grooves or projections to assist in indexing the adjustor 400. The rotation stop 212 can prevent rotation of adjustor 400 directly from any setting to any other setting without the deliberate intent of the doctor. This can also mimic the rotational limits on the valve rotor 110.

The upper 210 and lower 220 rings interface at rotation joint 214. In particular, the upper ring 210 has an upper ring joint 214A and the lower ring has a lower ring joint 214B. The joint 214 allows the upper and lower rings 210, 220 to rotate relative to each other. In particular, allowing the lower ring 220 to remain fixed, while the upper ring 210 is rotated relative to lower 220. This rotation can be both clockwise and counter-clockwise and can be unlimited, other examples have rotation in one direction, or less than 360°.

The lower ring 220 has a skin contact surface 216 opposite the upper ring 210, where the locator 200 contacts the patent. The lower ring 220 also has an indicator key or lock 218, which is described in more detail below. Additionally, between the joint 214 and the skin surface 216 can be telescopic section 222. The telescopic section 222 can increase the height H of the lower ring 220 in the direction away from the skin 102. The telescopic section 222 can be a series of nesting segments that can expand and collapse into each other. In an example, the telescoping section 222 only displaces vertically. It does not rotate to expand or contract. The reason for this is to allow for the indicator 300 to be displaced far enough to be zeroed while still nested. Thus, in one example, the height H can expand from 0 cm to approximately 15 cm (~0 inches to ~6 inches). Once zeroed at the distance, the telescoping section 222 can be collapsed so the indicator 300 can read the valve 100.

Figure 6:
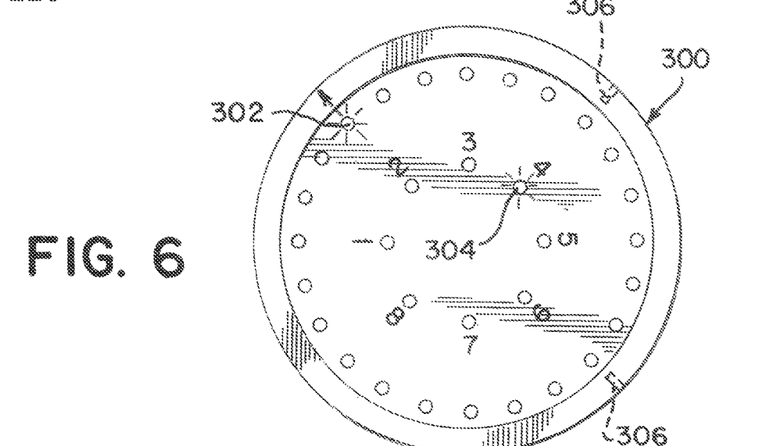
FIG. 6 is a top view of an example of the indicator of the present invention.

Turning now to the indicator 300, it can be used to determine the flow direction F and the position of the rotor 110. An example of the indicator 300 is illustrated in FIG. 6 and can include a flow position identifier 302, a rotor position identifier 304, and one or more key points 306 on an opposite side of the two identifiers 302, 304. The indicator 300 can be sized to nest or fit inside of the locator 200 and the two are used in conjunction to determine the relevant information regarding the valve 100.

The indicator 300 is zeroed (in a process described below) and inserted into the locator 200. The keys 218 on the locator 200 and the key points 306 are aligned so that the indicator 300 cannot rotate relative to the locator 200 once inserted. The flow position identifier 302 reads the magnetic field from at least the fixed magnetic marker 106 and indicates the direction of flow F which is also the orientation of the valve 100. The rotor position identifier 304 similarly reads the position of the rotor 110 and between the two readings, the setting of the valve 100 can be determined.

In examples of the valve 100, the settings of the rotor 110 can only understood once orientated to the flow direction F. Each of the different positions of the rotor 110 relative to the flow direction F is a different flow setting. Just knowing the absolute position of the rotor 110 does not provide enough information to determine the valve setting.

Figure 7:
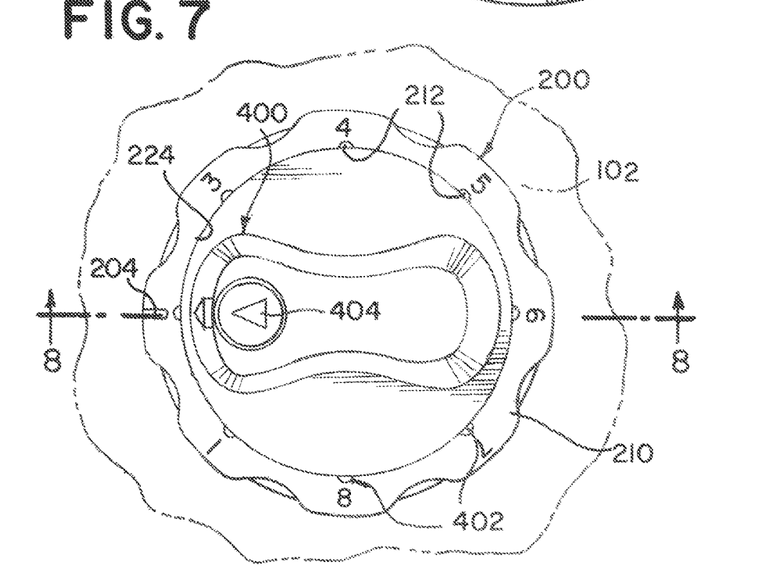
FIG. 7 is a top plan view of the adjuster nested within the locator.
Figure 8:
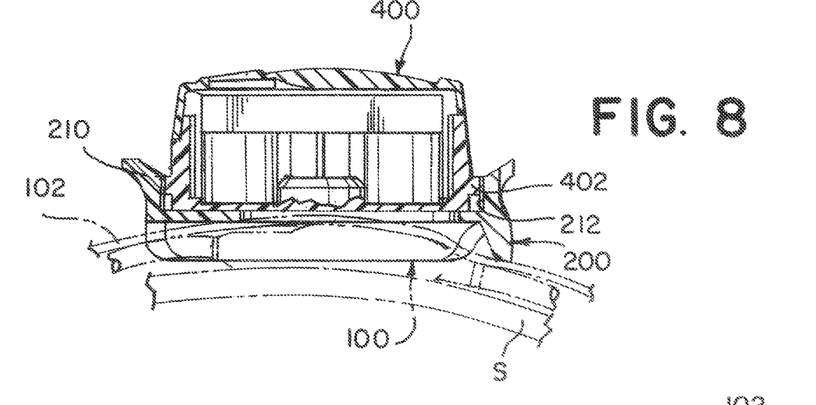
FIG. 8 is a partial cross-sectional view along lines 8-8 of FIG. 7.

Turning to FIGS. 7 and 8, the adjustor 400 is illustrated nested in the locator 200 and additional features on the locator 200 can be utilized with the adjuster tool 400. An interior 224 of the upper ring 210 defines a series of rotation stops 212 each of which can receive a detent 402 on the adjuster 400. It is desirable to have a least one of a tactile and audible indication, such as a click sound and/or feel, as the detent 402 engages one of the rotation stops 212. As noted, the flared surface can carry the pressure valve indicia 206 such as the lowest and highest pressure setting.

Figure 9A:
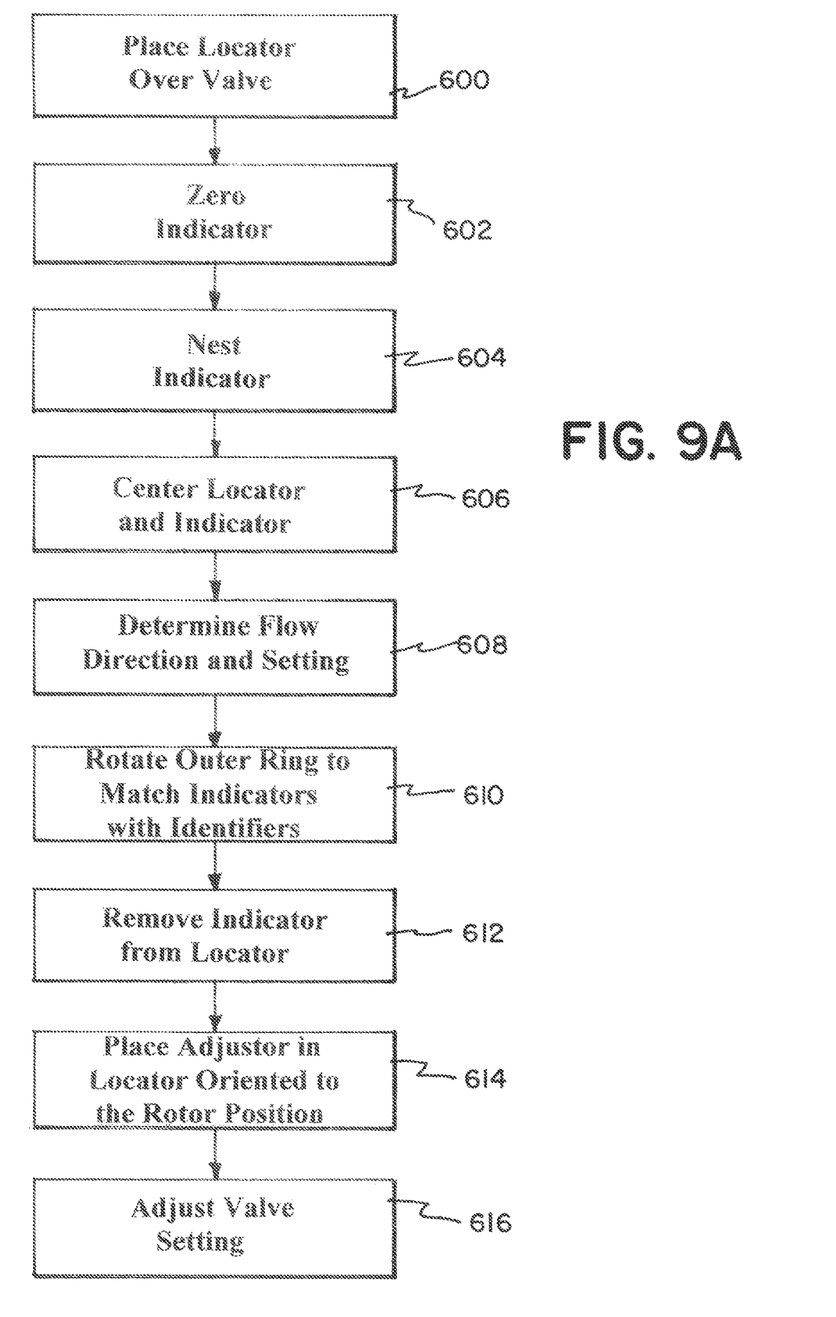
FIGS. 9A and 9B are a flow diagram of methods of using the toolkit of the present invention.

An example of the method and use of the toolkit 500, particularly the locator 200, can be illustrated in FIGS. 9-12 and described below. FIG. 9A illustrates the steps of an example of the method. First the locator 200 can be placed over the valve 100 (FIG. 10) (step 600). Generally, in one example the skin 102 is not palpitated, in other examples it can be lightly palpitated to position the center 202 of the locator 200 within 5 mm of the center/magnetic axis 104 of the valve 100. The orientation of the locator 200 to the position or flow direction F of the valve 100 is not considered during placement. Said diffidently, the locator 200 can be placed in any orientation over the valve 100. Next, the indicator 300 is zeroed (step 602) prior to being nested into the locator 200. This is known in the art, and can involve holding the indicator 300 approximately 10-15 cm above the valve 100 in order to take into account the earth's magnetic field. The indicator 300 is then nested (step 604) into the locator 200 and the user can start taking measurements regarding, at least, flow direction and valve setting. When the indicator 300 is nested, the key points 306 on the indicator 300 need to match up with the keys 218 on the locator 200. This orientates the indicator 300 in the locator 200. In a different example, the indicator 300 can first be nested and then zeroed by telescoping the lower ring 220 of the locator 200.

Figures 10, 11A:
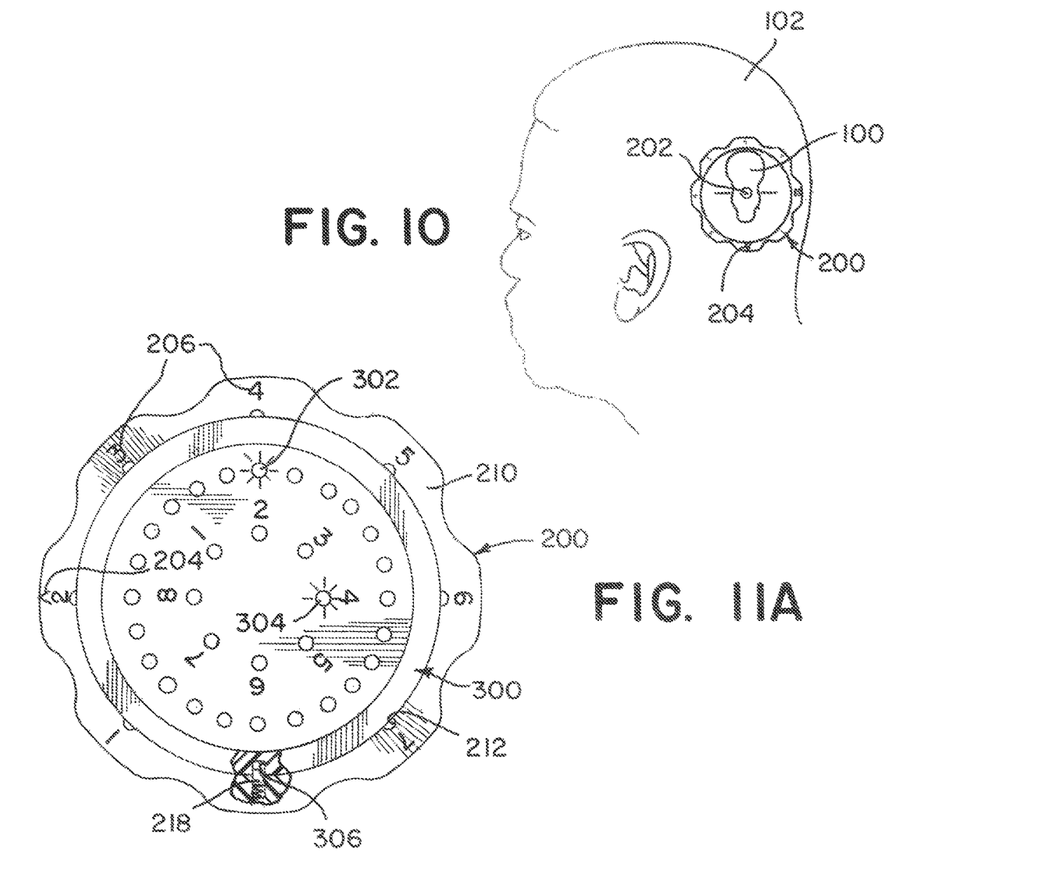
FIG. 10 illustrates an example of the placement of the locator over a patient's valve.
FIGS. 11A and 11B illustrate the calibration of the locator with the indicator.
Figure 11B:
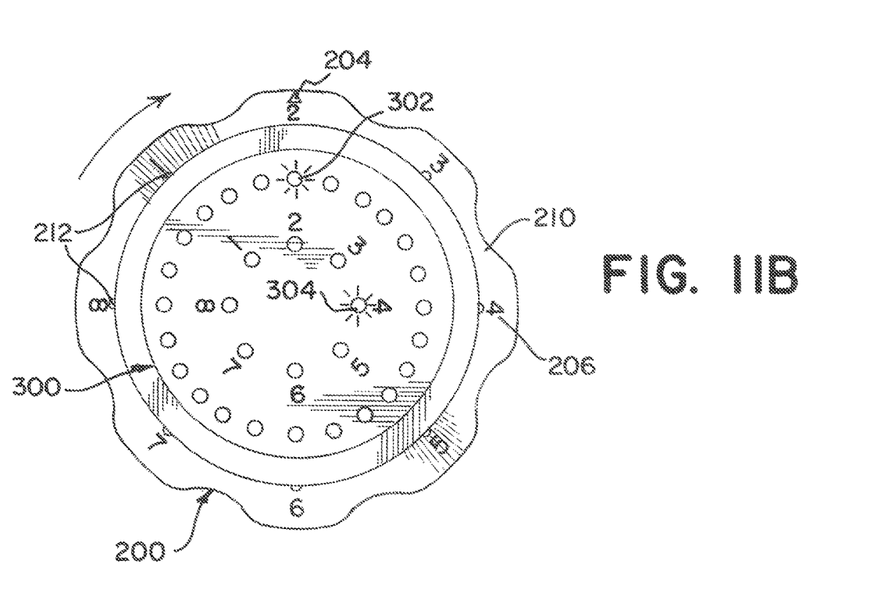

Once nested, the locator 200 and indicator 300 can be slowly moved on the skin 102, based on the readings of the flow position identifier 302 and/or the rotor position identifier 304 until the center 202 of the locator is centered over the magnetic axis 104 of the valve 100 to assure proper readings and valve adjustment (step 606). Once the pair 200, 300 is centered, the flow position identifier 302 can read the magnetic marker 106 to determine the flow direction F and the rotor position identifier 304 can read the position of the rotor 110 to determine the valve's setting (step 608). FIG. 11A illustrates the condition where the pair 200, 300 is centered, but the outer ring 210 is not aligned with the readings 302, 304 on the indicator 300. This can be because of the general nature of the placement of the locator 200. The outer ring 210 can be rotated to align the flow direction indicator 204 with the flow position identifier 302 and flow setting indicators 206 with the rotor position identifier 304 (step 610). This is illustrated in FIG. 11B and this example shows that the outer ring 210 can be rotated clockwise to align the indicators 204, 206 with the identifiers 302, 304. While the outer ring 210 is rotated, the inner ring 220, along with the indicator 300 remain fixed and do not rotate. This is a time saver, as in the prior art, if the orientation of the locator/indicator pair 200, 300 is off and the absolute orientation of the indicator 300 changed, the indicator 300 needs to be re-zeroed.

Figure 12:
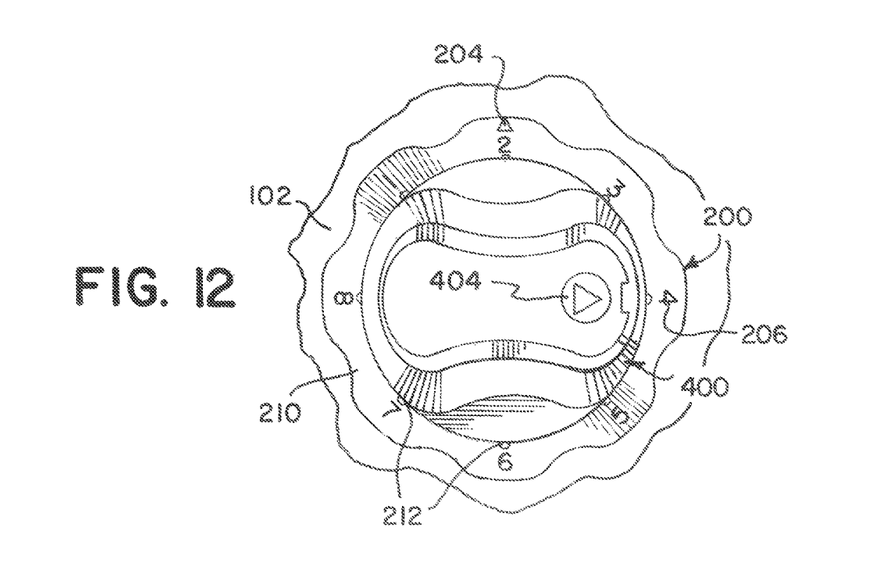
FIG. 12 illustrates the adjustor nested in the locator.

Now to complete the setting on the valve 100, the indicator 300 can be removed from the locator 200 (step 612), again taking care not to move the locator 200 relative to the center 202 and magnetic axis 106. The adjustor 400 is then disposed in locator 200 so that an adjustment arrow 404 points to the flow setting indicator 206 on the locator 200 which corresponds to the actual, current valve setting, as identified by the rotor position identifier 304 (step 614) (FIG. 12). Finally, rotate the adjustor 400 so that the adjustment arrow 404 points to a new flow setting indicator 206 on the locator 200 to change the valve setting (step 616).

After the desired setting is reached, the adjustor 400 is lifted directly away from the locator 200 without further rotation. Preferably, the indicator 300 is then replaced into the locator 200 and another reading is taken to confirm correct valve pressure setting. Alternatively or in addition to re-use of the indicator tool, the implanted valve 100 can be imaged with x-ray to confirm current valve setting.

Figure 9B:
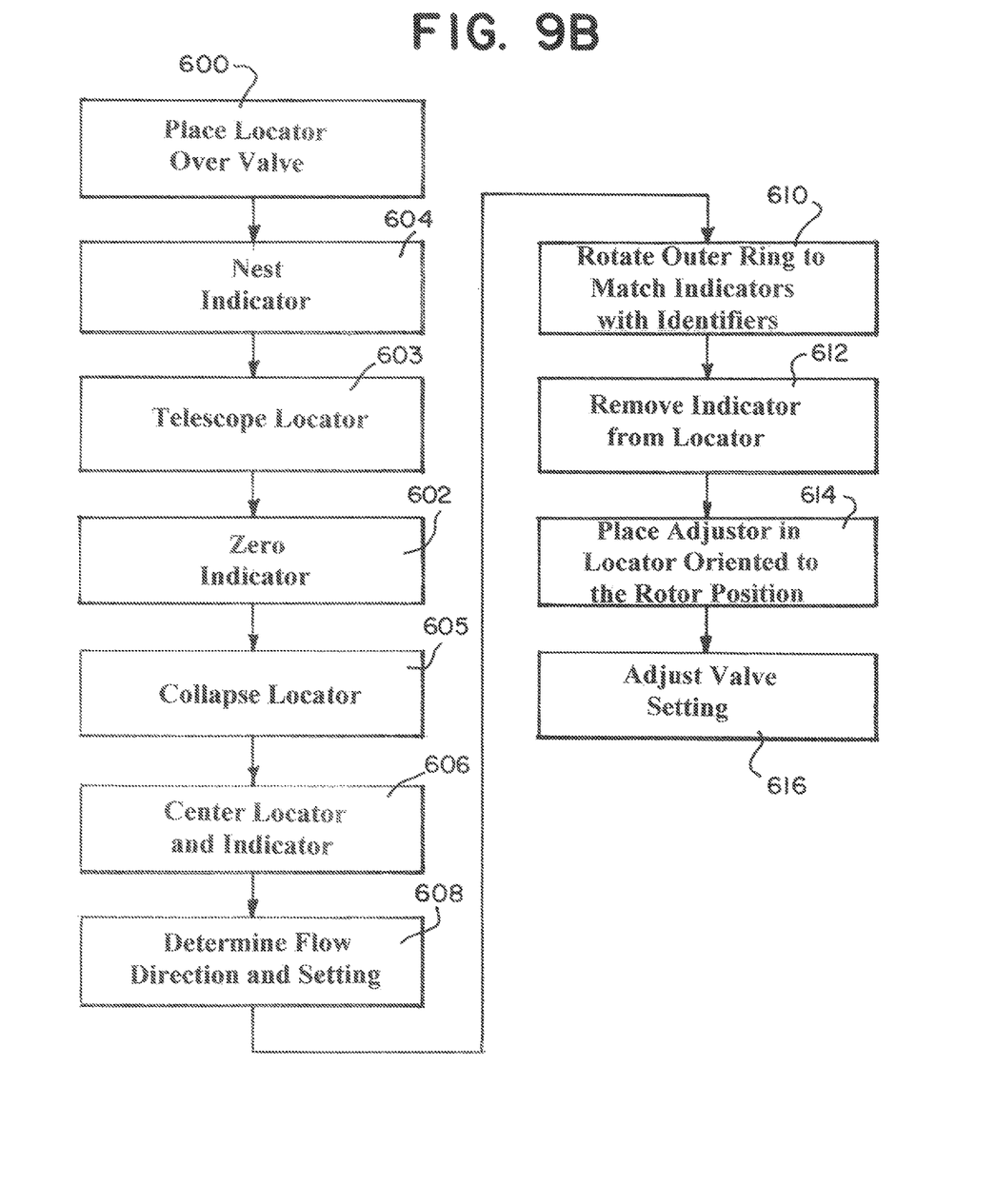

FIG. 9B illustrates a separate example of the method and use of the toolkit 500, particularly the locator 200, can be illustrated in FIGS. 9-12 and described below. FIG. 9 illustrates the steps of an example of the method. First the locator 200 can be placed over the valve 100 (FIG. 10) (step 600). The indicator 300 is then nested into the locator 200 (step 604) and the locator 300 is telescoped (step 603) to a distance approximately 10 cm to 15 cm from the valve 100. Next, the indicator 300 is zeroed (step 602) and then the locator 300 is collapsed so it can take the measurements from the valve 100 (step 605). The remaining steps are as above, the locator 200 and indicator 300 can center to assure proper readings and valve adjustment (step 606). Once centered, the valve's settings are determined (step 608). The outer ring 210 can be rotated to align the flow direction indicator 204 with the flow position identifier 302 and flow setting indicators 206 with the rotor position identifier 304 (step 610). Now to complete the setting on the valve 100, the indicator 300 can be removed from the locator 200 (step 612), again taking care not to move the locator 200 relative to the center 202 and magnetic axis 106. The adjustor 400 is then disposed in locator 200 so that an adjustment arrow 404 points to the flow setting indicator 206 on the locator 200 which corresponds to the actual, current valve setting, as identified by the rotor position identifier 304 (step 614). Finally, rotate the adjustor 400 so that the adjustment arrow 404 points to a new flow setting indicator 206 on the locator 200 to change the valve setting (step 616).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A locator for use with a toolkit for locating an implanted valve and configured for use in concert with an indicator that nests therein, the locator comprising:
    a lower ring, comprising:
        a contact surface configured for contacting a patient;
        a key extended inwardly radially from an inner nesting indicator surface, the key being configured to align with key points of the nested indicator to prevent rotation; and
        a lower ring joint opposite the contact surface; and
    an upper ring, comprising:
        an upper ring joint rotatingly interfacing with the lower ring joint;
        a flow direction identifier opposite the upper ring joint and comprising a visual indicator of flow direction that is identifiable through the implanted valve; and
        a flow setting identifier opposite the upper ring joint and denoting settings of the implanted valve;
    wherein the upper and the lower rings rotate relative to each other, and
    wherein the lower ring is floor-less.

2. The locator of claim 1, wherein the lower ring further comprises a telescoping section expanding and collapsing a height of the lower ring between the contact surface and the lower ring joint, wherein the telescoping section only moves vertically.

3. A method of using a toolkit for locating an implanted valve, the toolkit comprising a locator, comprising:
    an upper and a lower ring rotatably engaged to each other, wherein the upper ring comprises:
        an upper ring joint rotatably engaged with a lower ring joint that is opposite a contact surface of the lower ring; and
        a flow direction identifier opposite the upper ring joint and comprising a visual indicator of flow direction that is identifiable through the implanted valve,
        a flow setting identifier opposite the upper ring joint and denoting settings of the implanted valve; and
    an indicator and an adjustor that nest within the locator, the method comprising the steps of:
    placing the locator generally over the implanted valve;
    nesting the indicator in the locator;
    centering the locator and the indicator over the implanted valve;
    determining a flow direction, based on the flow direction identifier, and a valve setting based on the flow setting identifier, of the implanted valve; and
    rotating the upper ring of the locator to match the determined flow direction and valve setting while maintaining a position of the lower ring.

4. The method of claim 3, further comprising the step of zeroing the indicator at a distance from the implanted valve prior to the nesting step.

5. The method of claim 3, further comprising the steps of:
    telescoping the locator after the nesting step;
    zeroing the indicator at a distance from the implanted valve; and
    collapsing a height of the lower ring of the locator after the zeroing step and before the centering step.

6. The method of claim 3, further comprising the steps of:
    removing the indicator from the locator;
    disposing the adjustor in the locator oriented to the determined valve setting; and
    adjusting the valve setting to a new valve setting by rotating the adjustor.

7. The method of claim 5, wherein the lower ring further comprises a telescoping section for expanding and collapsing a height of the lower ring between the contact surface and the lower ring joint, wherein the step of telescoping is by the telescoping section moving vertically.

8. The method of claim 7, wherein the telescoping section further comprises a series of nesting segments, the method further comprising:
    expanding and collapsing the nesting segments into each other.

9. The method of claim 3, wherein the flow direction identifier is an arrow aligned with fluid flow through the implanted valve.

10. The method of claim 3, wherein the upper ring comprises a rotation stop having grooves or projections configured to assist in indexing an adjustor nested within the locator.

11. The method of claim 3, wherein during the step of rotating the upper ring the position of the lower ring remains fixed.

12. The method of claim 3, further comprising:
positioning the flow setting identifier on an upper nesting surface of the upper ring, wherein the flow setting identifier comprising visual markings denoting settings of the implanted valve;
wherein the indicator is nested in the upper nesting surface of the upper ring of the locator.

13. The locator of claim 1, wherein the flow direction identifier is an arrow aligned with fluid flow through the implanted valve.

14. The locator of claim 1, wherein the flow direction identifier and the flow setting identifier comprise visual markings with petals or tabs extending outside a first perimeter of the upper ring.

15. The locator of claim 1, wherein the upper ring comprises a rotation stop having grooves or projections configured to assist in indexing an adjustor nested within the locator.

16. The locator of claim 1, wherein the lower ring remains fixed while the upper ring is rotated relative to the lower ring.

17. The locator of claim 1, wherein the flow setting identifier is positioned on an upper nesting surface of the upper ring for receiving the nested indicator, and
wherein the flow setting identifier comprises visual markings denoting settings of the implanted valve.

18. The locator of claim 17, wherein the visual markings comprise positions of a rotor of the implanted valve.

19. The locator of claim 2, wherein the telescoping section comprises a series of nesting segments configured to expand and collapse into each other.

20. A locator for use with a toolkit for locating an implanted valve and configured for use in concert with an indicator that nests therein, the locator comprising:
a lower ring, comprising:
a contact surface configured for contacting a patient;
a key extended from an inner nesting indicator surface, the key being configured to align with key points of the nested indicator to prevent rotation; and
a lower ring joint opposite the contact surface; and
an upper ring, comprising:
an upper ring joint rotatingly interfacing with the lower ring joint;
a flow direction identifier opposite the upper ring joint and comprising a visual indicator of flow direction that is identifiable through the implanted valve; and
a flow setting identifier opposite the upper ring joint and denoting settings of the implanted valve;
wherein the upper ring rotates relative the lower ring that is fixed.

* * * * *